US012369773B2

(12) United States Patent
Jensrud et al.

(10) Patent No.: US 12,369,773 B2
(45) Date of Patent: Jul. 29, 2025

(54) MEDICAL CLEANING VALVE

(71) Applicant: Boston Scientific Scimed, Inc., Maple Grove, MN (US)

(72) Inventors: Allyn Narcisse Jensrud, Milford, MA (US); Larry Edward Stanton, Burlington, MA (US); Colby Harris, Norfolk, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 19 days.

(21) Appl. No.: 18/151,118

(22) Filed: Jan. 6, 2023

(65) Prior Publication Data

US 2023/0157520 A1 May 25, 2023

Related U.S. Application Data

(63) Continuation of application No. 16/903,670, filed on Jun. 17, 2020, now Pat. No. 11,571,113.

(60) Provisional application No. 62/862,893, filed on Jun. 18, 2019.

(51) Int. Cl.
*A61B 1/00* (2006.01)
*A61B 1/12* (2006.01)

(52) U.S. Cl.
CPC ...... *A61B 1/00068* (2013.01); *A61B 1/00103* (2013.01); *A61B 1/00137* (2013.01); *A61B 1/121* (2013.01)

(58) Field of Classification Search
CPC ............ A61B 1/00068; A61B 1/00103; A61B 1/00137; A61B 1/121
See application file for complete search history.

(56) References Cited

U.S. PATENT DOCUMENTS

| 4,537,209 | A | * | 8/1985 | Sasa ..................... A61B 1/125 134/102.1 |
| 5,938,589 | A | | 8/1999 | Wako et al. |
| 9,307,890 | B2 | * | 4/2016 | Ouchi ..................... A61B 1/05 |
| 2021/0204797 | A1 | * | 7/2021 | Hernandez ......... A61B 1/00055 |

FOREIGN PATENT DOCUMENTS

WO 2019040888 A1 2/2019

* cited by examiner

*Primary Examiner* — Michael J Carey
*Assistant Examiner* — Megan Elizabeth Monahan
(74) *Attorney, Agent, or Firm* — Seager, Tufte & Wickhem, LLP

(57) ABSTRACT

A medical valve may comprise a valve stem and an operation portion. The operation portion may include a stationary portion, a movable portion which is movable relative to the stationary portion and fixed relative to the valve stem, a seal disposed between the stationary portion and the movable portion, and a biasing member. Movement of the movable portion in a first direction may cause deformation of the biasing member, such that a restorative force of the biasing member urges movement of the movable portion in a second direction opposite the first direction. A frictional force between the seal and one of the stationary portion and the movable portion resists the movement of the movable portion in the second direction.

20 Claims, 8 Drawing Sheets

MEDICAL CLEANING VALVE

CROSS-REFERENCE TO RELATED APPLICATIONS

This application is a continuation of U.S. patent application Ser. No. 16/903,670, filed on Jun. 17, 2020, which claims the benefit of priority from U.S. Provisional Application No. 62/862,893, filed on Jun. 18, 2019, each of which is incorporated by reference herein in its entirety.

TECHNICAL FIELD

The present disclosure relates generally to valves for medical devices, particularly endoscopes.

BACKGROUND

Endoscopes include functionality to deliver fluids (including air and water) and suction to a site of a procedure. Tubing for delivering fluids and/or suction extends from a handle of the endoscope, through a sheath of the endoscope, and to a distal tip of the endoscope. During a procedure, body fluids, tissues, or other material can build up in the tubing and, in some cases, lead to clogging of the tubing. In order to aid in reprocessing of reusable endoscopes between procedures, pre-processing is performed in an endoscopy suite. For example, water or other fluids are flushed through the tubing after the endoscope is removed from a patient, in order to clear debris from the air/water and/or suction tubing. One option for accomplishing such pre-processing is a reusable cleaning valve. The cleaning valve may be inserted into an air/water valve cylinder of an endoscope after the scope is removed from a patient. An operator may then depress a button of the cleaning valve for a predetermined amount of time (e.g., 30 seconds) to flush the air and/or water channels of the endoscope prior to further reprocessing of the endoscope. Such cleaning may require active intervention by an operator. A reusable cleaning valve must be subject to cleaning, itself, in between uses, which can add to reprocessing cost. Therefore, a need exists for valves capable of performing cleaning functions.

SUMMARY

In one example, a medical valve may comprise a valve stem and an operation portion. The operation portion may include a stationary portion and a movable portion. The movable portion may be movable relative to the stationary portion and fixed relative to the valve stem. A seal may be disposed between the stationary portion and the movable portion. The operation portion may further include a biasing member. Movement of the movable portion in a first direction may cause deformation of the biasing member, such that a restorative force of the biasing member urges movement of the movable portion in a second direction opposite the first direction. A frictional force between the seal and one of the stationary portion and the movable portion resists the movement of the movable portion in the second direction.

Any of the medical valves disclosed herein may include any of the following features. The biasing member may be a spring. The movable portion may be movable in the first direction from a first configuration to a second configuration. A relationship between the frictional force and the restorative force may be such that, after the movable portion is transitioned from the first configuration to the second configuration, the movable portion will automatically move in the second direction to return to the first configuration. A radially outer surface of the valve stem may include a first aperture and a second aperture. The valve stem may include a lumen extending along a longitudinal axis of the valve. The lumen may be in fluid communication with the first aperture and the second aperture. A proximal seal, a one-way seal, and three distal seals may be disposed on an outer surface of the valve stem. The first aperture may be between the proximal seal and the one-way seal. The second aperture may be between a first of the three distal seals and a second of the three distal seals. The valve may be movable in a proximal direction and a distal direction relative to a valve cylinder that receives the valve. The valve may be rotatable about a longitudinal axis of the valve and relative to a valve cylinder that receives the valve. A first and a second rotatable seal may be disposed on the valve stem. In a first configuration of the valve, a first hole in the first rotatable seal and a second hole in the second rotatable seal may face a first direction. In a second configuration of the valve, the first hole and the second hole may face a second direction different from the first direction. The valve may also include an O-ring seal between the first rotatable seal and the second rotatable seal. The first hole may be aligned with a first aperture in a radially outer surface of the valve stem. The second hole may be aligned with a second aperture in the radially outer surface of the valve stem. Each of the first and second rotatable seals may include a recessed notch extending partially around an outer circumference of the rotatable seal. The first hole may be within the recessed notch of the first seal. The second hole may be within the recessed notch of the second seal. The movable portion may include a rim that extends between inner and outer cylindrical portions of the stationary portion. The stationary portion may include a mating feature for mating with a valve cylinder of an endoscope. The valve stem may be a single, unitary structure formed of a single material.

In another example, a medical valve may comprise a movable portion movable between a first configuration and a second configuration; a stationary portion, a seal disposed between the stationary portion and the movable portion and providing a frictional force between the stationary portion and the movable portion; and a spring. Transitioning the movable portion from the first configuration to the second configuration may deform the spring. The deformed spring may exert a restorative force urging the movable portion back to the first configuration. A relationship between the frictional force and the restorative force may be such that, after the movable portion is transitioned from the first configuration to the second configuration, the movable portion will automatically return to the first configuration after an amount of time.

Any of the medical valves disclosed herein may include any of the following features. The valve may be movable in a proximal direction and a distal direction relative to a valve cylinder that receives the valve. The valve may be rotatable about a longitudinal axis of the valve and relative to a valve cylinder that receives the valve.

A method for cleaning an endoscope may comprise providing a force to a valve to transition the valve from a first configuration in which water is not delivered to an air channel to a second configuration in which water is delivered to an air channel; and releasing the force. After the force is released, the valve may continue to deliver water to the air channel for an amount of time before automatically transitioning back to the first configuration.

Any of the methods disclosed herein may include the following steps or aspects. The valve may include a movable portion; a stationary portion; a seal disposed between the stationary portion and the movable portion and providing a frictional force between the stationary portion and the movable portion; and a spring. Transitioning the movable portion from the first configuration to the second configuration may deform the spring. The deformed spring may exert a restorative force urging the movable portion back to the first configuration. A relationship between the frictional force and the restorative force may be such that, after the movable portion is transitioned from the first configuration to the second configuration, the movable portion will automatically return to the first configuration after the amount of time.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to a surface used by an operator for operating a valve (e.g., a button) and the term "distal" means a direction away from the surface used by an operator for operating a valve (e.g., a button). Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the present disclosure and, together with the description, serve to explain the principles of the disclosure.

DETAILED DESCRIPTION

A valve may be configured to provide cleaning functionality to an air channel of an endoscope. In at least some embodiments, the valve may be appropriate for a single-use and therefore be disposable. In a first configuration, the valve may provide neither air nor water flow to air and/or water channels of an endoscope. In a second configuration, the valve may provide only water flow to only an air channel of the endoscope. The valve may include features that, after the valve is transitioned from the first configuration to the second configuration, retain the valve in the second configuration for a predetermined amount of time, such as a time specified for flushing an air valve in a cleaning protocol. Thus, the valve may be in a second, flushing configuration for a predetermined amount of time without active participation by a user, so that the user may perform other tasks during the flushing of the air channel of the endoscope. After the predetermined amount of time, the valve may transition from the second configuration back to the first configuration automatically.

Figure 1A:
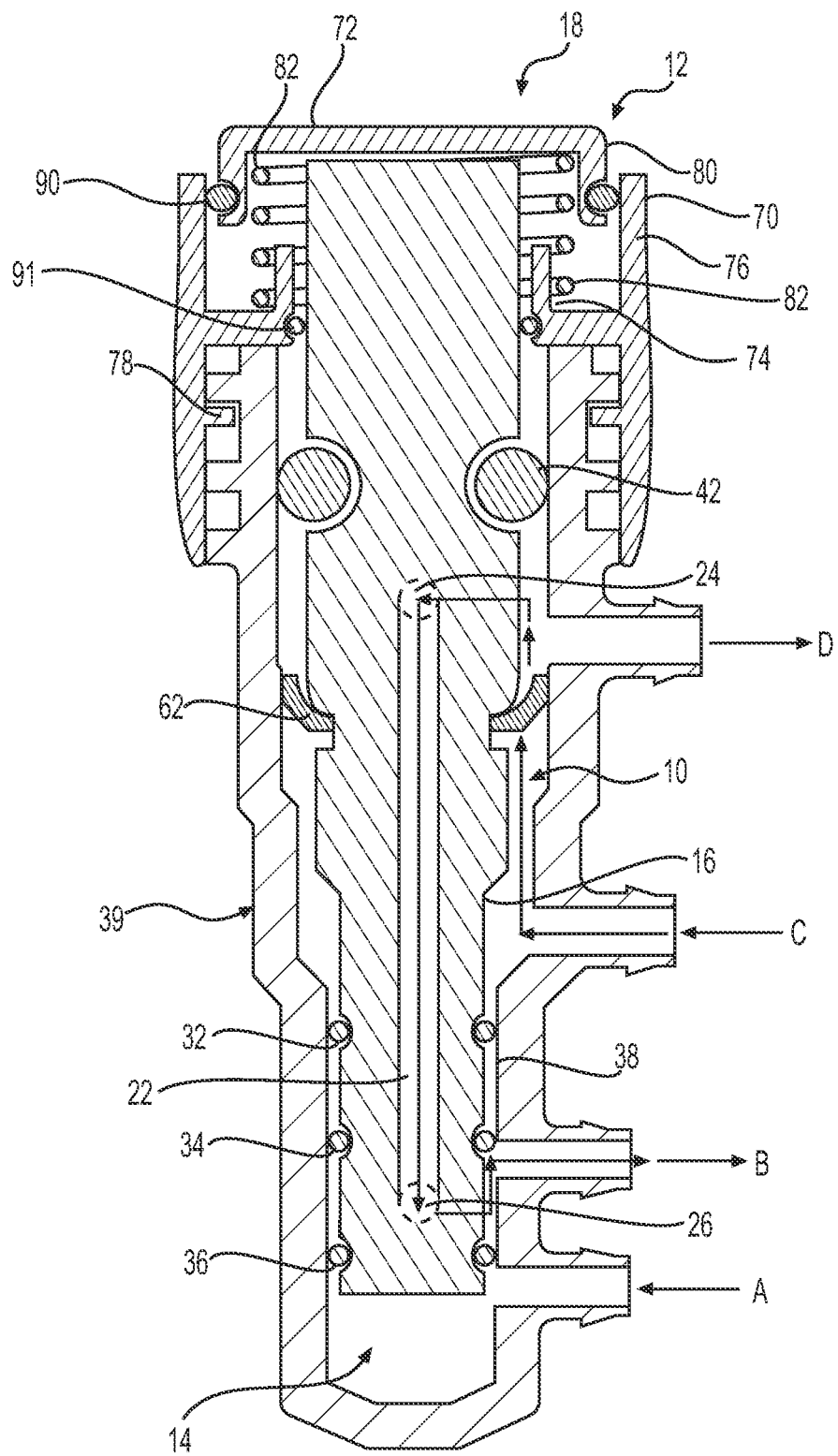
FIGS. 1A and 1B show cross-sectional views of a first exemplary valve.
Figure 1B:
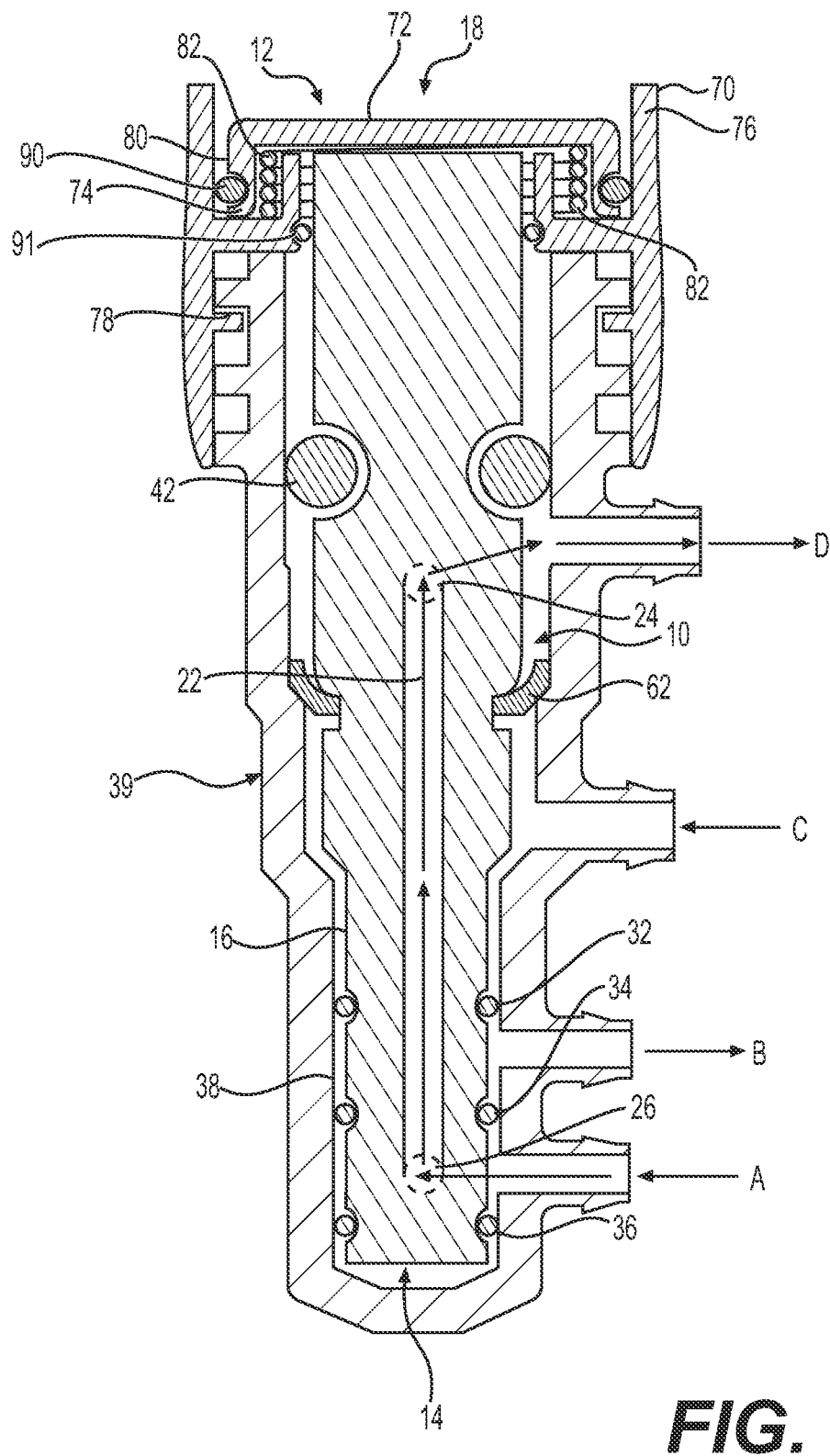

FIGS. 1A-1B show cross-sectional views of a first exemplary cleaning valve 10 in a valve cylinder 39. FIG. 1A shows valve 10 in a first configuration, and FIG. 1B shows valve 10 in a second configuration. Valve cylinder 39 may have a water inlet A, a water outlet B, an air inlet C, and an air outlet D. Water inlet A may be in fluid communication with a source of water or other liquid (e.g., water, cleaning solution, air, other gases, or combinations thereof). Water outlet B may be in fluid communication with a water channel of an endoscope (not shown), which may extend from a proximal end of the endoscope to a distal end of the endoscope. During a medical procedure, the water channel may be used to deliver water at a site of the procedure. Air inlet C may be in fluid communication with a source of air or other fluid (e.g., air, other gases, water, or cleaning solution, or combinations thereof). Air outlet D may be in fluid communication with an air channel of the endoscope. During a medical procedure, the air channel may be used to deliver air at a site of the procedure.

Valve 10 may have a proximal end 12 and a distal end 14. A valve stem 16 may extend from proximal end 12 to distal end 14. A cap 18 (which may be an operation portion of valve 10) may be disposed at proximal end 12. Valve stem 16 may be a single, unitary structure formed of a single, continuous piece of material and may be made from a metal (e.g., stainless steel, titanium, aluminum, etc.), from a polymer (e.g. polycarbonate, ABS, HDPE, Nylon, PEEK, thermoplastic, plastic, etc.), or from any other suitable material. Depending on the material used, valve stem 16 may be machined, injection molded, extruded (via, e.g., 3D printing), or otherwise formed. Valve stem 16 may be formed of a clear thermoplastic so that certain portions of an interior of valve stem 16 are visible through external walls of inner cylindrical member.

Valve stem 16 may have a lumen 22 extending through a central longitudinal axis of valve stem 16. Alternatively, lumen 22 may extend through another longitudinal axis of valve stem 16 (e.g., lumen 22 may be off-centered). A space between an exterior surface of valve stem 16 and a surface defining lumen 22 may be solid, and lumen 22 may be a bore formed in valve stem 16. In another example, a space between an exterior surface of valve stem 16 and a surface defining lumen 22 may be hollow. In such a case, lumen 22 may be formed by a longitudinal tube within valve stem 16.

Lumen 22 may be open to an exterior of valve stem 16 on a proximal end of lumen 22 via one or more proximal apertures 24. For example, lumen 22 may be fluidly connected to proximal aperture(s) 24 via a second, proximal lumen (not shown) which may be transverse to lumen 22. For example, the second lumen may be perpendicular to lumen 22 (extending into the page in FIG. 1A). Lumen 22 may be open to an area exterior of valve stem 16 on a distal end of lumen 22 via one or more distal apertures 26. Lumen 22 may be fluidly connected to distal aperture(s) 26 via a third, distal lumen (not shown) which may be transverse to lumen 22. For example, the third, distal lumen may be perpendicular to lumen 22 (extending into the page in FIG. 1A).

Valve stem 16 may have disposed on it a first distal seal 32, a second distal seal 34, and a third distal seal 36. Distal seals 32, 34, 36 may be made from elastomeric material. Distal seals 32, 34, 36 may be identical to one another and may be, for example, O-rings. Distal seals 32, 34, 36 may be disposed in circumferential, annular grooves or indentations on valve stem 16. A durometer value and outer diameter of distal seals 32, 34, 36 may be such that the distal seals 32, 34, 36 have an interference fit with an inner surface 38 of an endoscope valve cylinder 39 when valve 10 is inserted in endoscope valve cylinder 39. The interference fit may be loose enough so that valve stem 16 may slidably move relative to surface 38 but tight enough so that fluids cannot flow longitudinally between a radially outermost surface of seals 32, 34, 36 and surface 38. Third distal seal 36 may be disposed near to a distal end 14 of valve 10, distal to distal aperture 26. Second distal seal 34 may be proximal of third distal seal 36 and proximal to distal aperture 26. First distal seal 32 may be proximal of second distal seal 34 but still distal of proximal aperture 24.

Valve stem 16 may also have disposed on it a proximal seal 42. Proximal seal 42 may have any of the properties of distal seals 32, 34, 36. For example, proximal seal 42 may be an elastomeric O-ring and may be disposed in an annular circumferential groove or indentation of valve stem 16. A durometer value and outer diameter of proximal seal 42 may be such that the proximal seal 42 has an interference fit with surface 38 (see FIGS. 1A-1B) when valve 10 is inserted in endoscope valve cylinder 39. The interference fit may be loose enough so that valve stem 16 may slidably move relative to endoscope valve cylinder surface 39 but tight enough so that fluids cannot flow longitudinally between a radially outermost surface of proximal seal 42 and surface 38. Proximal seal 42 may have a larger inner diameter than distal seals 32, 34, 36 due to a small diameter of the groove within valve stem 16 at a location of proximal seal 42. Proximal seal 42 may have a larger outer diameter than distal seals 32, 34, 36 due to a wider space defined by surface 38 at the location of seal 42 compared to a space defined by surface 38 at the location of seals 32, 34, 36. It is understood that seals 32, 34, 36, and 42 may be any size to fit around the valve stem 16 and to seal against surface 38 to selectively prevent fluid flow.

Valve stem 16 may also be fitted with a one-way seal 62, which may be disposed longitudinally along the valve stem 16 between first distal seal 32 and proximal seal 42. One-way seal 62 may be formed of an elastomeric material, which may stretch to fit over valve stem 16. One-way seal 62 may be disposed in a groove or indentation of valve stem 16. An inner surface of one-way seal 62 may be sized so that there is a slight interference between an external surface of valve stem 16 and the inner surface of one-way seal 62, so that a tight seal is formed. An outer diameter of one-way seal 62 may be sized so as to form a slight interference fit with surface 38 (see FIGS. 1A-1B). A thin flap of one-way seal 62 may extend radially outward from valve stem 16 at an angle transverse to a longitudinal axis of valve stem 16. For example, the thin flap may extend at an angle between approximately 10 degrees and 80 degrees relative to a longitudinal axis of valve stem 16. The flap of one-way seal 62 may be expandable so that when fluid (e.g., water or air) moves in a distal direction, a positive pressure will expand the flap, maintaining a seal between one-way seal 62 and surface 38 (see FIGS. 1A-1B). Fluid moving proximally will also create a positive pressure, but the positive pressure will produce a force normal to a longitudinal axis of valve stem 16 to radially compress the flap of one-way seal 62 toward valve stem 16. Thus, fluid (e.g., air or water) is permitted to move proximally past one-way seal 62, between one-way seal 62 and surface 38.

Proximal aperture 24 may be disposed axially between one-way seal 62 and proximal seal 42. Distal aperture 26 may be disposed axially between third distal seal 36 and second distal seal 34.

Cap 18 may have a stationary portion 70 and a movable portion 72. Although movable portion 72 is described herein as being separate from valve stem 16, it will be appreciated that movable portion 72 and valve stem 16 could be formed of a single integral piece. Stationary portion 70 may remain stationary with respect to valve cylinder 39 when valve 10 is inserted in valve cylinder 39. Stationary portion 70 may include an inner cylindrical member 74 and an outer cylindrical member 76. As shown in FIGS. 1A-1B, inner cylindrical member 74 and outer cylindrical member 76 may be made from a single, unitary piece of material, which may facilitate manufacturing efficiencies. Alternatively, inner cylindrical member 74 and outer cylindrical member 76 may be two separate pieces that are assembled together. Outer cylindrical member 76 may include one or more mating features 78 for mating cap 18 with an outer portion of valve cylinder 39. For example, mating feature 78 may be a protrusion extending radially inward and matable with a corresponding groove or indentation of valve cylinder 39. A distal surface of inner cylindrical member 74 may rest upon a proximal outer surface of valve cylinder 39. A cross-section of inner cylindrical member 74 may be "L" shaped, forming a seat, for a spring (to be described, below).

Movable portion 72 may be proximally and distally (axially) movable relative to valve stem 16 and/or stationary portion 70. Movable portion 72 may be affixed to valve stem 16, so that proximal or distal (axial) movement of movable portion 72 also causes the same motion of valve stem 16. As discussed above, movable portion 72 may be integrally formed with valve stem 16. Movable portion 72 of cap 18 may have a button shape or any other suitable shape. A rim 80 of movable portion 72 may extend in a longitudinal direction between outer cylindrical member 76 and inner cylindrical member 74.

Cap 18 may be fitted with a spring 82, which may be a biasing member. Spring 82 may be a coil spring, leaf spring, or another type of resilient member, such as any member having shape-memory properties. Spring 82 may be, for example, a compression spring. Spring 82 may be configured in cap 18 so that, when spring 82 is in a relaxed state, valve 10 has a first configuration relative to stationary portion 70. When movable portion 72 is moved distally so that valve 10 has a second configuration, spring 82 may be in a deformed, compressed state and may store potential energy due to the deformation (e.g., compression) of spring 82. Spring 82 may have properties, including a stiffness, such that spring 82 exerts a known return force on movable portion 72 after it has been moved distally from the first configuration to the second configuration.

A cap seal 90 may be disposed between movable portion 72 and stationary portion 70. Cap seal 90 may be, for example, an O-ring seal, a washer, or other type of structure and may be formed of elastomeric material. Alternatively, something other than a seal that provides a resistive or frictional force between movable portion 72 and stationary portion 70 may be used in place of cap seal 90. For example, instead of cap seal 90, portions of movable portion 72 or stationary portion 70 may be textured or may have structures or substances disposed thereon that increase resistance between them. As shown in FIGS. 1A and 1B, cap seal 90 may be fixed to movable portion 72, in an annular groove within movable portion 72, and cap seal 90 is movable with respect to stationary portion 70. Alternatively, cap seal 90 may be fixed to stationary portion 70 and movable with respect to movable portion 72. Cap seal 90 may provide a frictional force between an outer surface of cap seal 90 and an inner surface of stationary portion 70. Thus, when valve 10 is in the second configuration, and spring 82 is in a deformed, compressed state, friction caused by cap seal 90 may resist a return force of spring 82 that urges movable portion 72 and valve stem 16 proximally to the first configuration, in which spring 82 is relaxed. The relationship between a frictional force caused by cap seal 90 and a return force caused by spring 82 may be such that valve 10 automatically moves from the second configuration to the first configuration in a set, predetermined amount of time. In other words, the frictional force may delay the return of valve 10 to the first configuration. The delay may align with a time desired to flush an air channel of an endoscope, as discussed below.

A stem seal 91 may be disposed between stationary portion 70 and valve stem 16. Stem seal 91 may be, for example, an O-ring seal, a washer, or other type of structure and may be formed of elastomeric material. As shown in FIGS. 1A and 1B, stem seal 91 may be fixed to stationary portion 70, in an annular groove within stationary portion 70, and stem seal 91 is movable with respect to valve stem 16. Alternatively, stem seal 91 may be fixed to valve stem 16 and movable with respect to stationary portion 70. Stem seal 91 may be configured such that fluids (e.g., air or water) cannot pass proximally or distally of stem seal 91.

FIG. 1A shows valve 10 in a first configuration, in which air is flushed through both a water channel and an air channel of an endoscope. In the first configuration, spring 82 may be in a relaxed state, and movable portion 72 may be in a raised position, as a result. In the first configuration, third distal seal 36 may be positioned proximal to a water inlet A of endoscope valve cylinder 39 and also distal to a water outlet B of endoscope valve cylinder 39. Second distal seal 34 may be proximal of water outlet B but distal to air inlet C. First distal seal 32 may also be distal to air inlet C. One-way seal 62 may be proximal of air inlet C and distal to air outlet D.

Thus, in the first configuration, water, or other fluid, from water inlet A may not move proximally past third distal seal 36 and may thus not move to water outlet B. Air, or other fluid, from air inlet C may not move distally along an outer surface of valve stem 16 due to first distal seal 32. However, air from air inlet C may move proximally past one-way seal 62. Air may thus pass into air outlet D and also into proximal aperture 24. Air that has passed into proximal aperture 24 may pass distally through lumen 22 and out of distal aperture 26. Because distal aperture 26 is between third distal seal 36 and second distal seal 34, the air exiting distal aperture 26 may not move proximally or distally along an outer surface of valve stem 16. However, the air exiting distal aperture 26 may exit the water outlet B. The first configuration may be used after flushing an air channel of an endoscope to ensure that water is removed from the air channel and the water channel before the scope is subject to further reprocessing.

FIG. 1B shows valve 10 in a second, compressed configuration, in which water is flushed down the air channel. Spring 82 may be compressed in the second configuration so that movable portion 72 is translated distally relative to the first configuration. An entirety of valve stem 16 is shifted distally by a same amount by which movable portion 72 is shifted. Proximal seal 42 may remain proximal of air outlet D. One-way seal 62 may be shifted distally relative to the first configuration, so that air or other fluid from air inlet C may not move past one-way seal 62 (e.g., fluid flow is prevented) because a distal portion of one-way seal 62 fits in a narrowed, tapered region of endoscope valve cylinder 39 so that air cannot flow proximally past the distal portion of one-way seal 62 to reach the proximal movable flap portion of one-way seal 62.

In the second configuration, third distal seal 36 may be distal to water inlet A, and second distal seal 34 may remain proximal of water inlet A. Therefore, water or other fluid from water inlet A may enter proximally of third distal seal 36 but may not move proximally past second distal seal 34 along an outer surface of valve stem 16. However, water or other fluid may enter distal aperture 26 and travel through lumen 22 and through proximal aperture 24. After water or other fluid exits proximal aperture 24, the water may not flow distally past one-way seal 62 or proximally past one-way seal 62. However, water or other fluid may flow out air outlet D to flush out the air channel of an endoscope.

If an operator releases movable portion 72 of cap 18 after transitioning valve 10 from the first configuration (FIG. 1A) to the second configuration (FIG. 1B), valve 10 will slowly move back to the first configuration due to restorative forces exerted by spring 82. However, valve 10 may not immediately return back to the first configuration due to frictional forces caused by cap seal 90. For example, cap seal 90 may exert forces opposite forces exerted by spring 82, thereby delaying relaxation of the spring 82 and return to the first configuration of the valve 10. Valve 10 may continue to deliver water or other fluid to air outlet D until third distal seal 36 passes proximally of water inlet A. Thus, valve 10 may deliver water or other fluid to air outlet D for a predetermined amount of time, which may be specified by a cleaning protocol, without a user pressing on portion 72 of cap 18. For example, cap seal 90 and spring 82 may be calibrated so as to flush an air channel for a particular, predetermined amount of time.

After a procedure using an endoscope is completed, an operator may remove an air/water valve used during the procedure from valve cylinder 39. The operator may then insert valve 10 into valve cylinder 39. Distal portion 76 cap 18 may be secured to valve cylinder 39 using mating feature 78.

Valve 10 may be inserted into valve cylinder 39 in the first configuration of valve 10. An operator may press down movable portion 72, which compresses spring 82, and shifts valve stem 16 downward, relative to valve cylinder 39 and stationary portion 70. The user may then release movable portion 72 and may attend to other aspects of a postoperative procedure. Even without operator intervention, valve 10 may be maintained in the second, compressed configuration for a predetermined amount of time (e.g., thirty seconds) so as to flush water through an air channel of the endoscope, thereby removing debris from the air channel. As discussed above, interactions between spring 82 and cap seal 90 may facilitate automatically flushing water for a predetermined amount of time. Movable portion 72 (and valve stem 16) may eventually return to the first configuration due to a force exerted by spring 82, as discussed above. Following completion of flushing of water through the air channel, valve 10 may be disposed.

Figure 2A:
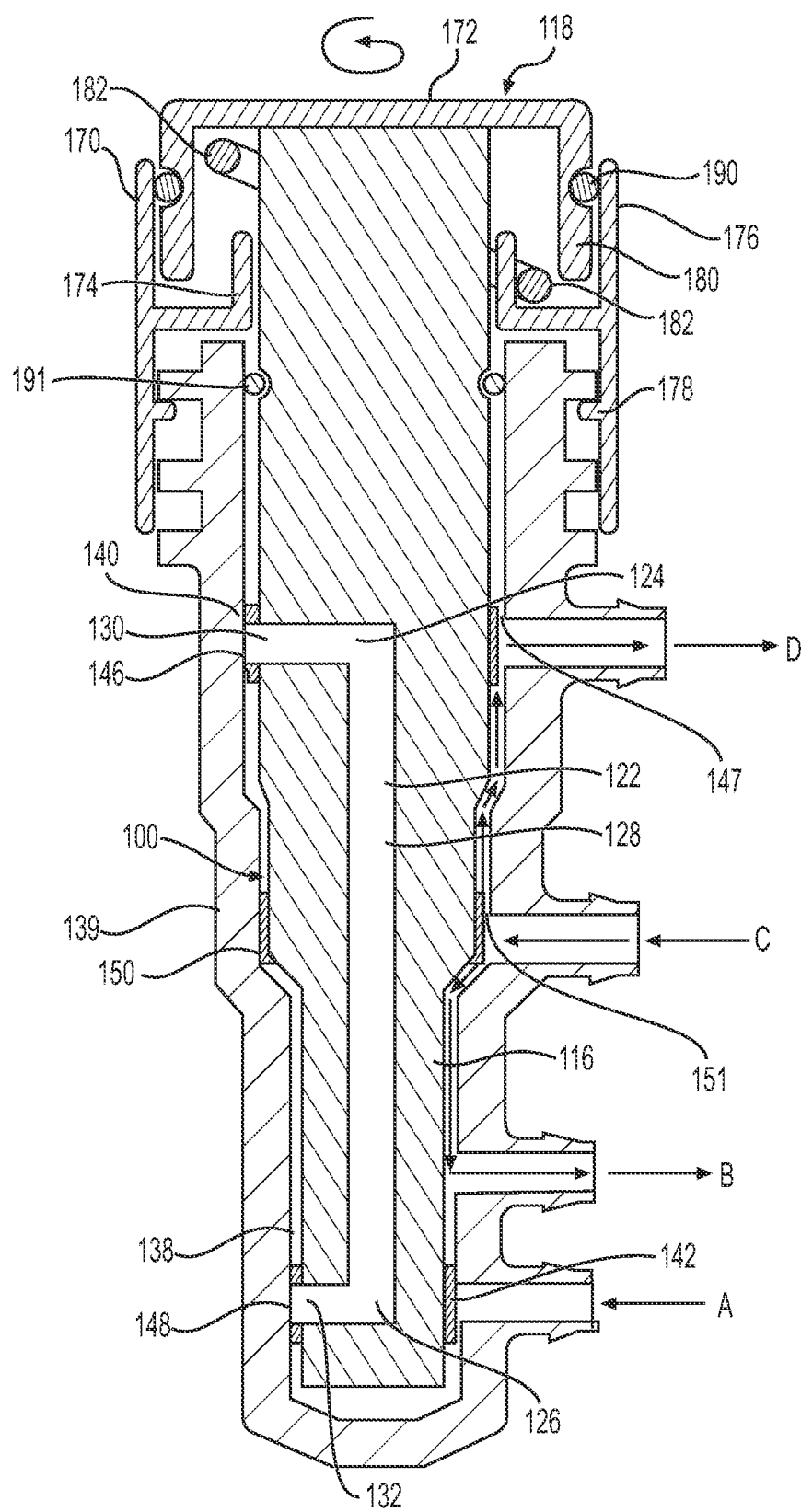
FIGS. 2A and 2B show cross-sectional views of a second exemplary valve.
Figure 2B:
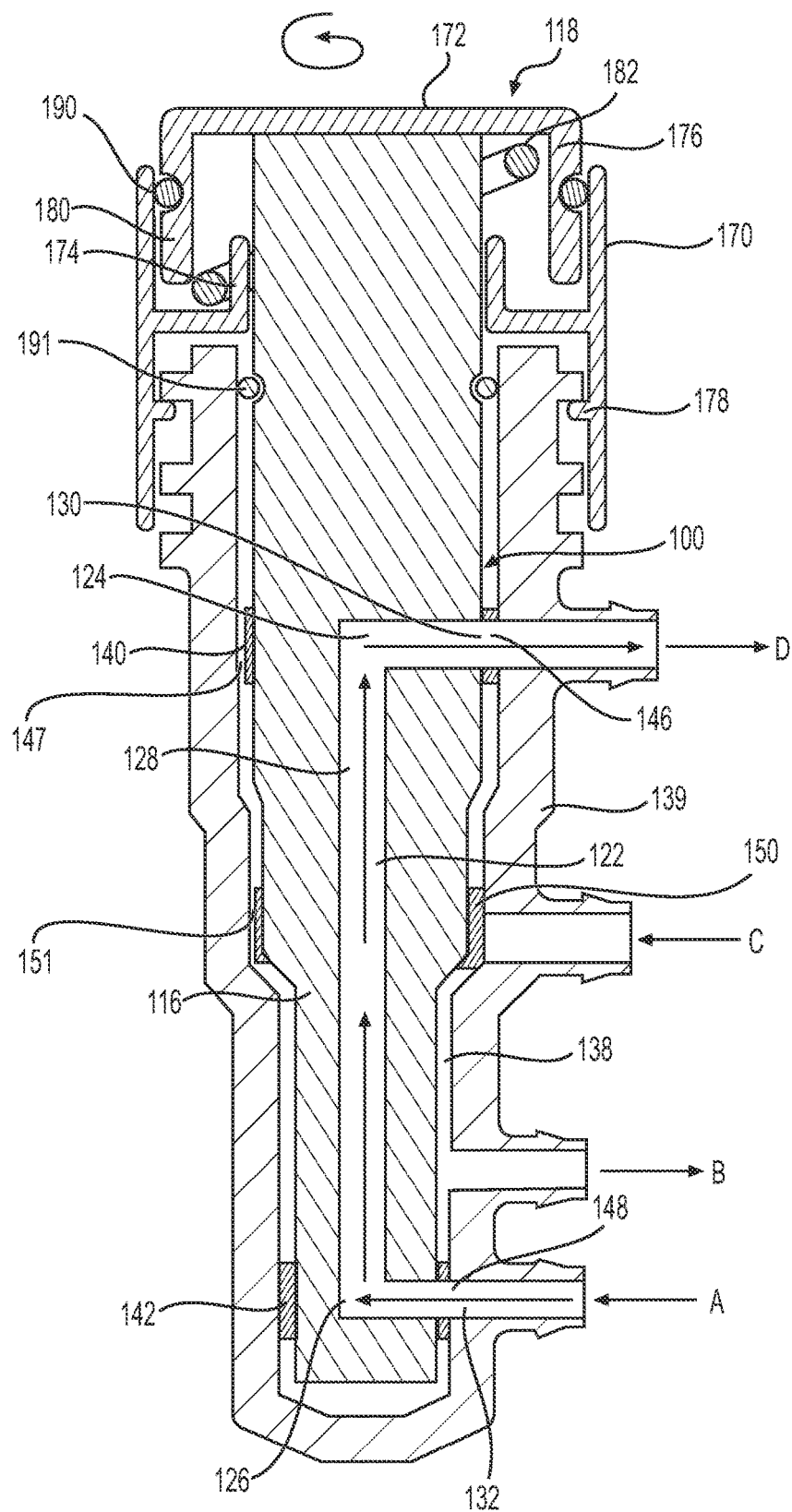

Turning to FIGS. 2A and 2B, a second exemplary valve 100 may include a valve stem 116 and a cap 118 (which may be an operation portion of valve 100). Valve 100 may be installed into a valve cylinder 139, which may have any of the properties of valve cylinder 39. Valve 100 may have any of the properties of valve 10.

Valve stem 116 may be formed of any suitable material, including any of those outlined above with respect to valve stem 16 and may have any of the properties of valve stem 16. Valve stem 116 may include a lumen 122, which may have any of the properties of lumen 22. Lumen 122 may be substantially formed along a central longitudinal axis of valve stem 116 or along another, off-center longitudinal axis of valve stem 116. Alternatively, at least a portion of lumen 122 may be transverse to a longitudinal axis of valve stem 116. Lumen 122 may have a proximal bend 124 and a distal bend 126. A midsection 128 of lumen 122 may be between proximal bend 124 and distal bend 126. Lumen 122 may bend up to 90 degrees, approximately 90 degrees, or any other suitable amount at proximal bend 124 and/or distal bend 126. A proximal end of lumen 122 may terminate at a proximal opening or aperture 130. Proximal opening 130 may extend through a wall of valve stem 116 and may cause lumen 122 to be in fluid connection with an area exterior to valve stem 116. A distal end of lumen 122 may terminate at a distal opening or aperture 132. Distal opening 132 may extend through a wall of valve stem 116 and may cause lumen 122 to be in fluid connection with an area exterior to valve stem 116. Proximal opening 130 and distal opening 132 may be radially aligned on valve stem 116. Proximal bend 124 and/or distal bend 126 may be omitted. If proximal bend 124 is omitted, proximal opening 130 may be in direct communication with midsection 128 of lumen 122. Similarly, if distal bend 126 is omitted, distal opening 132 may be in direct communication with midsection 128 of lumen 122. Valve stem 116 may be fitted with a proximal rotation seal 140, a distal rotation seal 142, and a middle rotation seal 150.

Figure 3A:
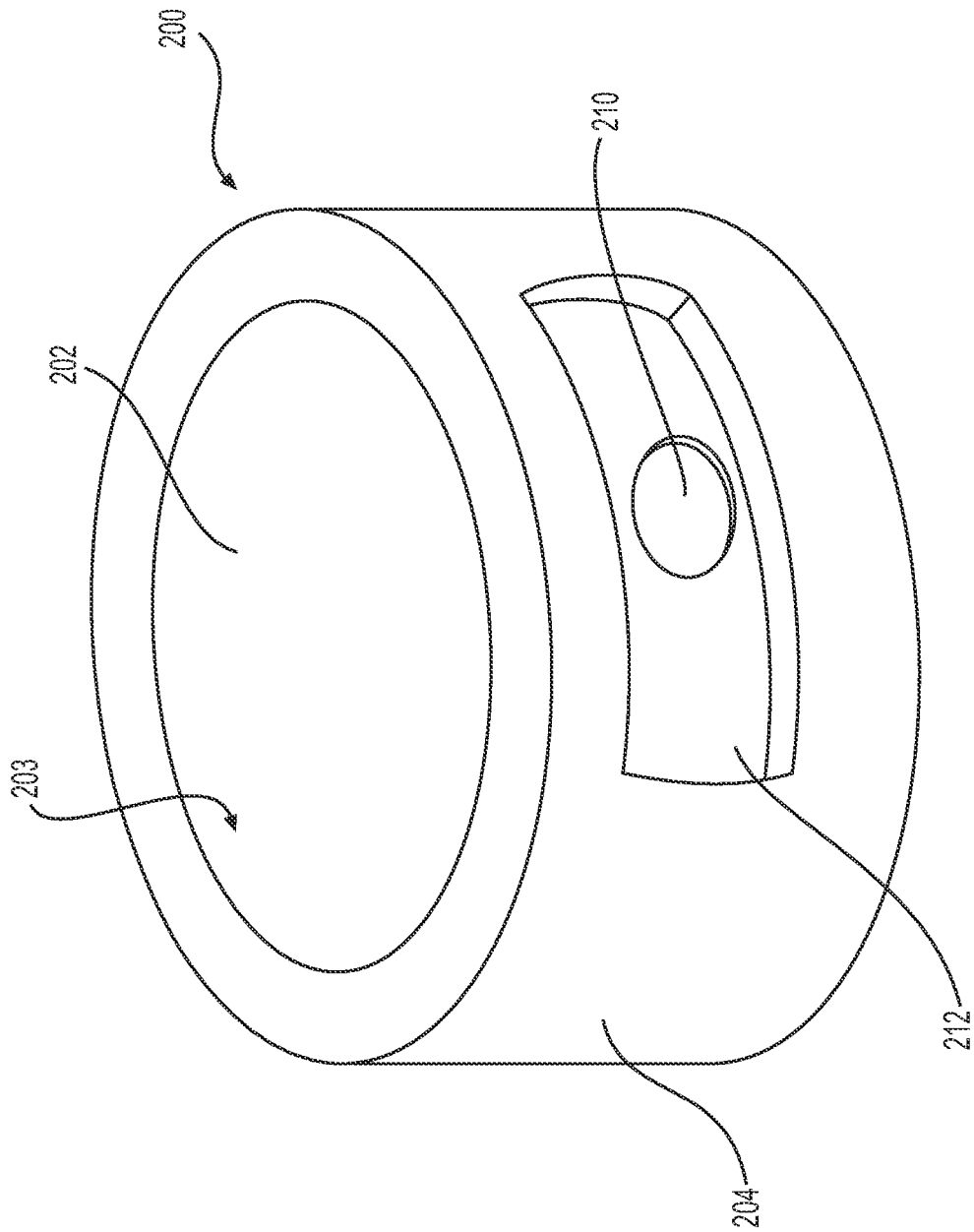
FIGS. 3A-3D show exemplary seals that may be used in conjunction with the second exemplary valve of FIGS. 2A and 2B.

FIG. 3A shows an exemplary seal 200, the basic structure of which may be used for distal rotation seal 142. Seal 200 or features of seal 200 may also be used for proximal rotation seal 140 and/or middle rotation seal 150. Seal 200 may be made from any appropriate material, and may be elastomeric. As shown in FIG. 3A, seal 200 may be annular and may have a roughly washer or O-ring shape. Seal 200 may have an inner opening 202 defined by an inner surface 203. Surface 203 may be fit around a circumference of valve stem 116 so that inner surface 203 is in contact with an outer surface of valve stem 116. An outer surface 204 of seal 200 may contact inner surface 138 of valve cylinder 139, when valve 100 is inserted into valve cylinder 139. Surfaces 203 and 204 may be flat; in other words, a wall defining opening 202 may have a substantially uniform thickness, except in the areas of a hole 210 and a notch 212 to be described. Hole 210 may be formed through a wall of seal 200, extending from a surface defined by notch 212 to inner surface 203. Outer surface 204 of seal 200 may define a recessed notch 212, which may surround hole 210. Notch 212 may have an have a substantially rectangular cross-section and may extend at least partially around a circumference outer surface 204, past hole 210. Notch 212 may extend circumferentially past hole 210 in both directions (as shown) or only in one direction or the other (e.g., notch 212 may terminate near hole 210). Notch 212 may have a similar width (in an axial direction) to a diameter of hole 210, or notch 212 may have a width (in an axial direction) that is smaller than a diameter of hole 210. Notch 212 may have a thickness (in a radial direction) such that it extends partially through a wall defining opening 202 but not entirely through the wall defining opening 202. A function of notch 212 will be discussed in further detail below.

Figure 3B:
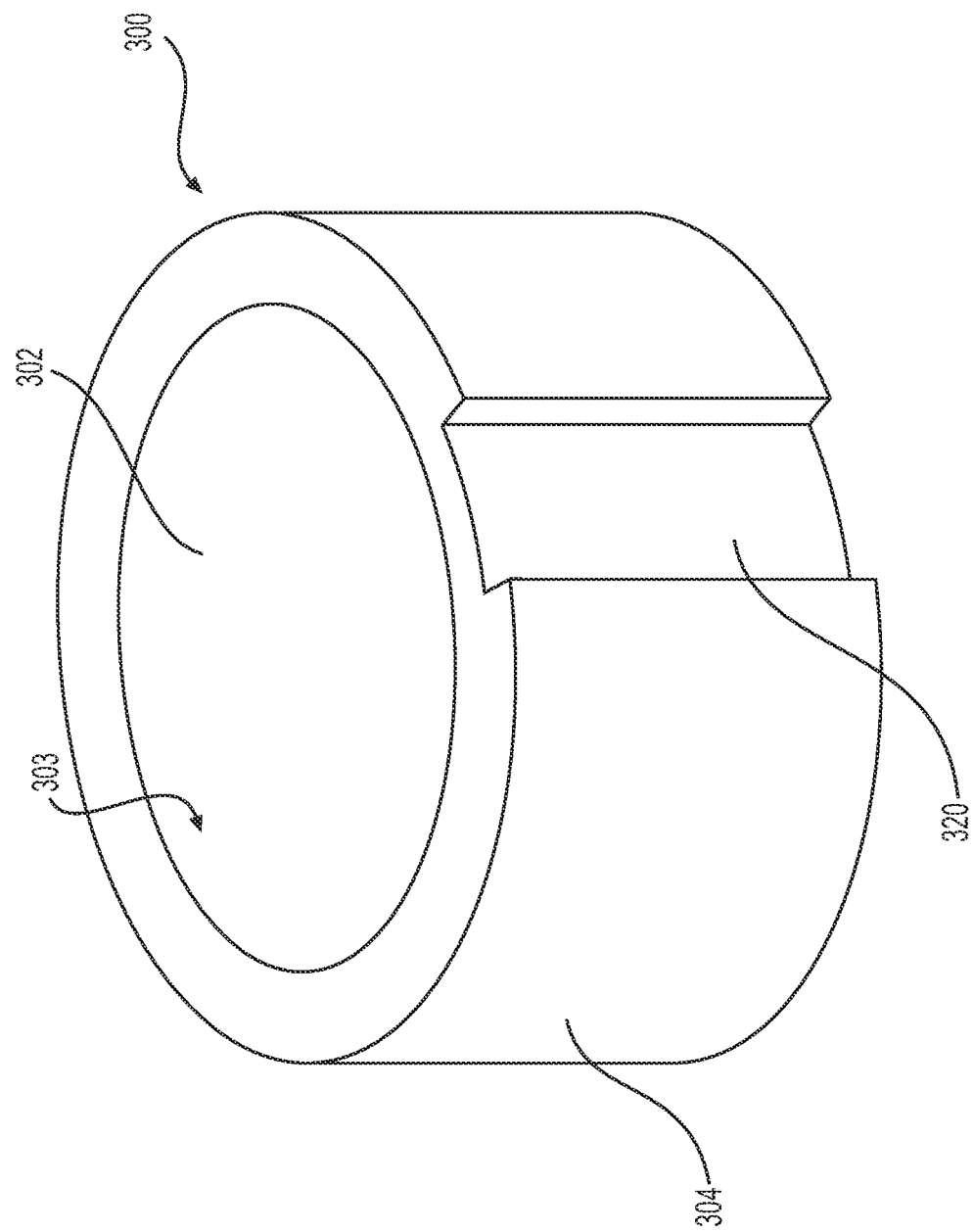

FIG. 3B shows an exemplary seal 300, the basic structure of which may be used for middle rotation seal 150. Seal 300 may have any of the features of seal 200, discussed above. Seal 300 or features of seal 300 may also be used for proximal rotation seal 140 and/or distal rotation seal 142. Seal 300 may be made from any appropriate material, and may be elastomeric. As shown in FIG. 3B, seal 300 may be annular and may have a roughly washer or O-ring shape. Seal 300 may have an inner opening 302 defined by an inner surface 303. Surface 303 may be fit around a circumference of valve stem 116 so that inner surface 303 is in contact with an outer surface of valve stem 116. An outer surface 304 of seal 300 may contact inner surface 138 of valve cylinder 139, when valve 100 is inserted into valve cylinder 139. Surfaces 303 and 304 may be flat; in other words, a wall defining opening 302 may have a substantially uniform thickness, except in the areas of a notch 320 to be described. Outer surface 304 of seal 300 may define a recessed notch 320, which extend along a longitudinal length of seal 300. Notch 320 may have an have a substantially rectangular cross-section. A function of notch 320 will be discussed in further detail below. Alternatively, seal 300 may not have a full annular shape and may instead extend around only a portion of a circumference of valve stem 116. In such a configuration, notch 320 may be omitted from seal 300.

Figure 3C:
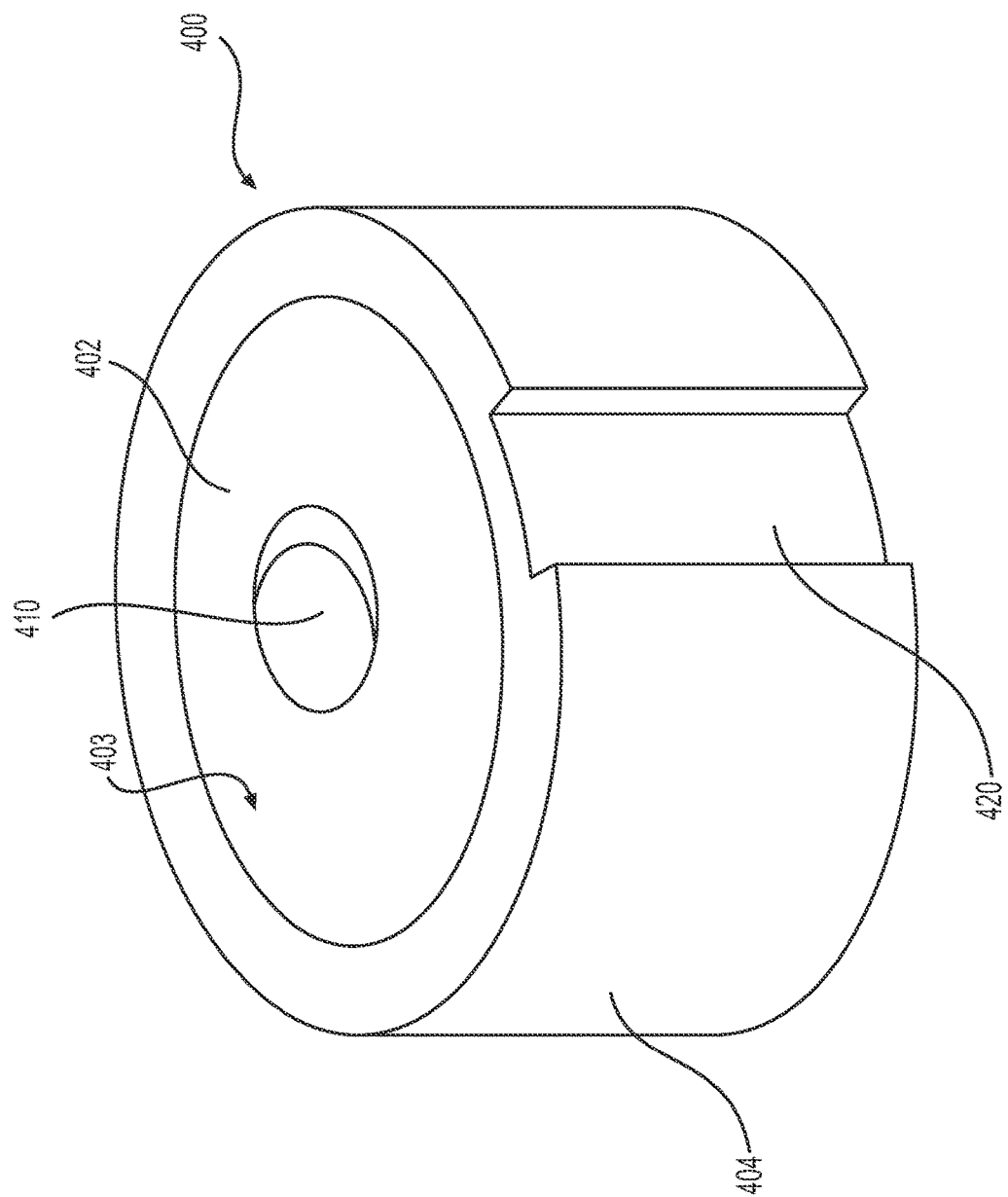
Figure 3D:
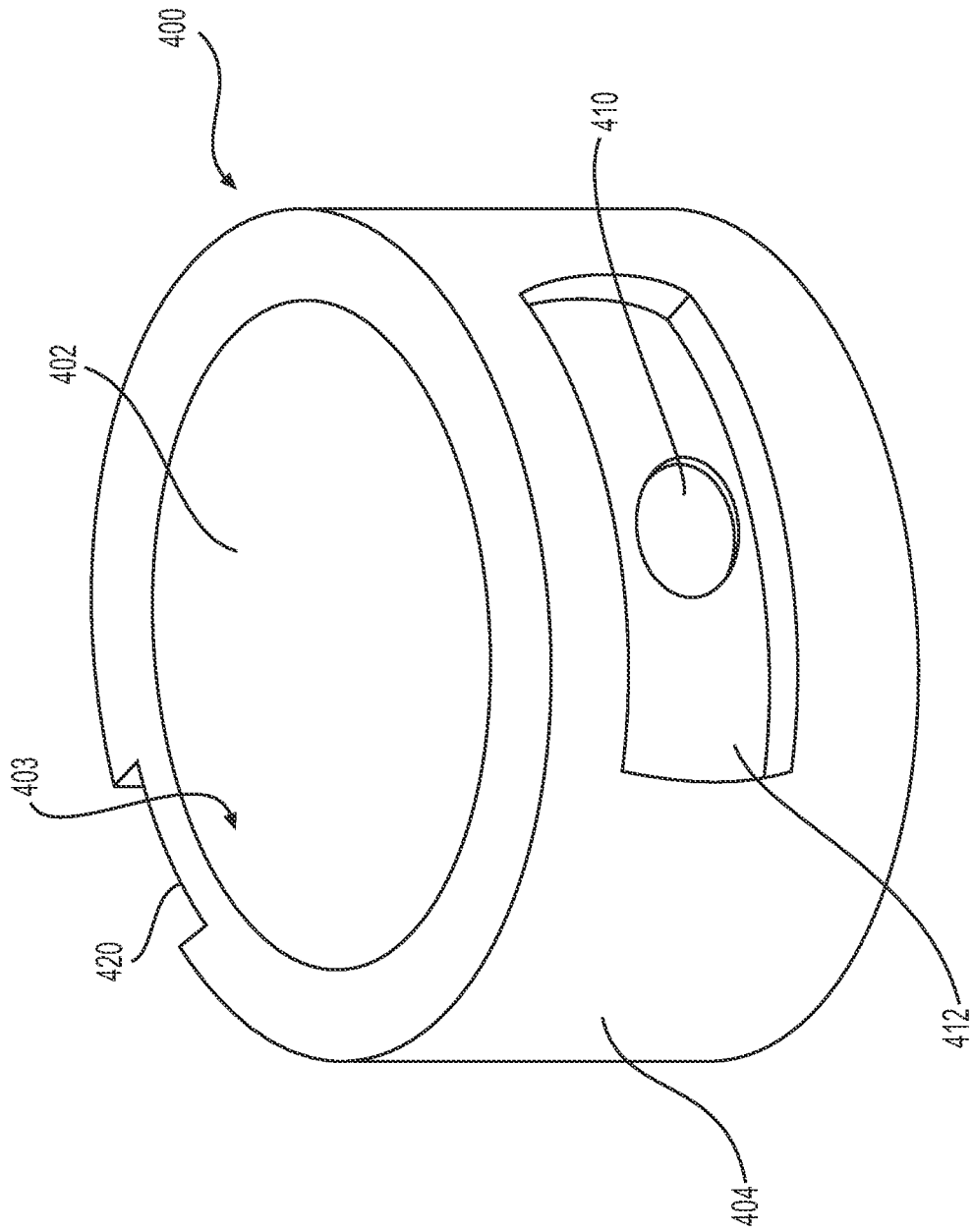

FIGS. 3C and 3D show another exemplary seal 400, the basic structure of which may be used for proximal rotation seal 140. Seal 400 may have any of the features of seals 200, 300, discussed above. Seal 400 or features of seal 400 may also be used for distal rotation seal 142 and/or middle rotation seal 150. Seal 400 may be made from any appropriate material, and may be elastomeric. Seal 400 may be annular and may have a roughly washer or O-ring shape. Seal 400 may have an inner opening 402 defined by an inner surface 403. Surface 403 may be fit around a circumference of valve stem 116 so that inner surface 403 is in contact with an outer surface of valve stem 116. An outer surface 404 of seal 200 may contact inner surface 138 of valve cylinder 139, when valve 100 is inserted into valve cylinder 139. Surfaces 403 and 404 may have any of the features of surfaces 303, 304, discussed above. Hole 410 may be formed through a wall of seal 400, extending from a surface defined by notch 412 to inner surface 403. Outer surface 404 of seal 400 may define a recessed notch 412, which may surround hole 410. Hole 410 and notch 412 may have any of the features of hole 210 and notch 212, respectively, as discussed above. Outer surface 404 of seal 400 may define a recessed notch 420, which extend along a longitudinal length of seal 400. Notch 420 may have any of the properties of notch 320, discussed above. Notch 420 may be disposed diametrically opposite of hole 410 or at another angle relative to hole 410. Alternatively, seal 400 may not have a full annular shape and may instead extend around only a portion of a circumference of valve stem 116. In such a configuration, notch 420 may be omitted from seal 400.

As discussed above, proximal rotation seal 140, distal rotation seal 142, and middle rotation seal 150 may have features of seals 200, 300, 400, discussed above. Proximal rotation seal 140, distal rotation seal 142, and middle rotation seal 150 may have different inner and/or outer diameters, in order to accommodate different diameters of valve stem 116 and/or valve cylinder 139 at the respective locations of proximal rotation seal 140 and distal rotation seal 142.

Proximal rotation seal 140 (which may have any of the structures described above, with respect to seal 400), may be positioned so that a hole 146 (which may have any of the properties of hole 410) of proximal rotation seal 140 aligns with proximal opening 130. A notch 147 of proximal rotation seal 140 (which may have any of the properties of notch 420) may be positioned so that it is 180 degrees (diametrically opposed) from proximal opening 130 or at a different angle relative to proximal opening 130 (as discussed below).

Distal rotation seal 142 (which may also have any of the structures described above, with respect to seal 200) may be positioned so that a hole 148 (which may have any of the properties of hole 210) of distal rotation seal 142 aligns with distal opening 132. Thus, lumen 122 may be in fluid communication with an exterior surface of proximal rotation seal 140 and distal rotation seal 142, via holes 146 and 148, respectively.

Middle rotation seal 150 (which may also have any of the structures described above, with respect to seal 300) may be positioned so that a notch 151 (which may have any of the properties of notch 320) is positioned in line with notch 147 of proximal rotation seal 140. Middle rotation seal may be positioned 180 degrees (diametrically opposed from) proximal opening 130 and distal opening 132, or at another angle relative to proximal opening 130 and distal opening 132 (as discussed below).

Proximal rotation seal 140, distal rotation seal 142, and middle rotation seal 150 may be configured so that each has a slidable interference fit with an inner surface 138 of valve cylinder 139 when seals 140, 142, 150 are positioned about valve stem 116. Fluids, such as air and/or water, may not move proximally or distally past distal rotation seal 142, between an outer surface of valve stem 116 and an inner surface 138 of valve cylinder 139. Fluids, such as air and/or water, may not move proximally or distally past proximal rotation seal 140 or middle rotation seal 150, between an outer surface of valve stem 116 and an inner surface 138 of valve cylinder 139, except at notch 147, 151, respectively.

Cap 118, which may have any of the properties of cap 18, may include a stationary portion 170 and a rotatable portion 172. Although rotatable portion 172 is described herein as being separate from valve stem 116, it will be appreciated that rotatable portion 172 could be formed integrally with valve stem 116. Stationary portion 170 may remain stationary with respect to valve cylinder 139 when valve 100 is inserted in valve cylinder 139. Stationary portion 170 may include an inner cylindrical member 174 and an outer cylindrical member 176. As shown in FIGS. 2A-2B, inner cylindrical member 274 and outer cylindrical member 276 may be made from a single, unitary piece of material, which may facilitate manufacturing efficiencies. Alternatively, inner cylindrical member 274 and outer cylindrical member 276 may be two separate pieces that are assembled together. Outer cylindrical member 176 may include one or more mating features 178 for mating cap 118 with an outer portion of valve cylinder 139. For example, mating feature 178 may be a protrusion extending radially inward that may mate with a corresponding groove or indentation of valve cylinder 139. A distal surface of inner cylindrical member 174 may rest upon a proximal outer surface of valve cylinder 139. A cross-section of inner cylindrical member 174 may be "L" shaped, forming a radially-outward directed flange, or seat, for a spring (to be described).

Rotatable portion 172 may be rotatable relative to valve cylinder 139 and/or stationary portion 170. Although rotatable portion 172 is described separately from valve stem 116, it will be understood that rotatable portion 172 and valve stem 116 could be formed of a single, integral structure. Rotatable portion 172 may be affixed to valve stem 116, so that rotation of rotatable portion 172 also causes rotation of valve stem 116. Rotatable portion 172 of cap 118 may have a button shape, a knob shape, or any other suitable shape. An exterior surface of rotatable portion 172 may have gripping surfaces to assist a user in gripping onto rotatable portion 172. A rim 180 of rotatable portion 172 may extend in a longitudinal direction between outer cylindrical member 176 and inner cylindrical member 174. Rotatable portion 172 may also be proximally and distally movable. Rotatable portion 172 may rotate while it is being translated proximally or distally. For example, a user could press down on rotatable portion 172, which could engage a ramp or other surface and cause rotatable portion 172 to rotate as it translates proximally or distally.

Cap 118 may be fitted with a spring 182, which may be a biasing member. Spring 182 may be a coil spring, leaf spring, or another type of resilient member, such as any member having shape-memory properties. Spring 182 may be, for example, a torsion spring. Alternatively, spring 182 may be a compression spring. Spring 182 may be configured in cap 118 so that, when spring 182 is in a relaxed state, valve 100 has a first configuration. When rotatable portion 172 is rotated (e.g., in a clockwise or counterclockwise direction) about a longitudinal axis of the valve, so that valve 100 has a second configuration, spring 182 may be in a deformed state and may store potential energy due to the deformation of spring 182. Spring 182 may have properties, including a stiffness, such that spring 182 exerts a known return force on rotatable portion 172, after it has been rotated from the first configuration to the second configuration.

A cap seal 190 may be disposed between rotatable portion 172 and stationary portion 170. Cap seal 190 may have any of the properties of cap seal 90. Alternatively, something other than a seal that provides a resistive or frictional force between movable portion 172 and stationary portion 170 may be used in place of cap seal 190. For example, instead of cap seal 190, portions of movable portion 172 or stationary portion 170 may be textured or may have structures or substances disposed thereon that increase resistance between them. Cap seal 190 may be, for example, an O-ring seal, a washer, or other shape and may be formed of elastomeric material. As shown in FIGS. 2A and 2B, cap seal 190 may be fixed with respect to rotatable portion 172 in an annular groove within rotatable portion 172, and cap seal 190 may be rotatable with respect to stationary portion 170. Alternatively, cap seal 190 may be fixed with respect to stationary portion 170 and rotatable with respect to rotatable portion 172. Cap seal 190 may provide a frictional force between an outer surface of cap seal 190 and an inner surface of stationary portion 170. Thus, when valve 100 is in the second configuration, and spring 182 is in a deformed state, friction caused by cap seal 190 may resist a return force of spring 182 that urges valve 100 to the first configuration, in which spring 182 is relaxed. The relationship between a frictional force caused by cap seal 190 and a return force caused by spring 182 may be such that valve 100 automatically moves from the second configuration to the first configuration in a set, predetermined amount of time. In other words, the frictional force may delay the return of valve 100 to the first configuration. The delay may align with a time desired to flush an air channel of an endoscope, as discussed below.

A stem seal 191 may be disposed between valve stem 116 and inner surface 138 of valve cylinder 139. Stem seal 191 may be, for example, an O-ring seal, a washer, or other type of structure and may be formed of elastomeric material. Stem seal 191 may be fixed to valve stem 116. Stem seal 191 may be configured such that fluids (e.g., air or water) cannot pass proximally or distally of stem seal 191.

FIG. 2A shows valve 100 positioned in valve cylinder 139 and in the first configuration described above. Spring 182 is in a relaxed, neutral state so that spring 182 does not exert a force to rotate rotatable portion 172 and valve stem 116.

Proximal rotation seal 140 may be positioned so that hole 146 axially aligns with air outlet D but is angularly offset (relative to a longitudinal axis) from air outlet D. For example, hole 146 may be offset by 180 degrees or another angle (e.g., 90 degrees or 45 degrees) from air outlet D. FIG. 2A shows hole 146 as being offset from air outlet D by 180 degrees. Similarly, distal rotation seal 142 may be positioned so that hole 148 axially aligns with water inlet A but is angularly offset (relative to a longitudinal axis) from water inlet A. For example, hole 148 may be offset by 180 degrees or another angle (e.g., 90 degrees or 45 degrees) from water inlet A. FIG. 2A shows hole 148 as being offset from water inlet A by 180 degrees. Holes 146 and 148 may be offset from air outlet D and water inlet A, respectively, by the same angle (e.g., 180 degrees).

Proximal rotation seal 140 may further be positioned so that notch 147 is axially and radially aligned with air outlet D. Middle rotation seal 150 may also be positioned so that notch 151 is axially and radially aligned with air inlet C.

In the first configuration, water or other fluid from water inlet A may not pass proximally past distal rotation seal 142. Thus, water or other fluid may not exit either water outlet B or air outlet D. Air or other fluid from inlet C may pass proximally and distally past middle rotation seal 150 because notch 151 is aligned with air inlet C. Thus, air or other fluid may move distally and exit through water outlet B. Air or other fluid may also pass proximally past proximal rotation seal 140 because notch 147 is aligned with air outlet D. Thus, in the first configuration, air or other fluid passes from air inlet C through both water outlet B and air outlet D. The first configuration may be used after flushing an air channel of an endoscope to ensure that water is removed from the air channel and the water channel before the scope is subject to further reprocessing.

FIG. 2B shows valve 100 in the second configuration, discussed above. To transition valve 100 from the first configuration to the second configuration, a user may rotate rotatable portion 172 of cap 118. For example, as shown in FIGS. 2A-2B, rotatable portion 172 may be rotated by 180 degrees to transition valve 100 from the first configuration to the second configuration. Alternatively, rotatable portion 172 may be rotated by another amount, which may be equivalent to an offset of holes 146, 148 in the first configuration. In the second configuration, hole 146 of proximal rotation seal 140 may be axially and radially (angularly) aligned with air outlet D, and notch 147 may not be aligned with air outlet D. Similarly, hole 148 of distal rotation seal 142 may be axially and radially aligned with water inlet A. Middle rotation seal 150 may be rotated so that notch 151 no longer aligns with air inlet C.

In the second configuration, water or other fluid from water inlet A may pass through hole 148 and through distal opening 132 and into lumen 122. Water or other fluid may travel proximally through lumen 122, through proximal opening 130, through hole 146, and into air outlet D. Water or other fluid from water inlet A may not pass proximally past distal rotation seal 142. Water or other fluid exiting hole 146 may not pass distally past proximal rotation seal 140. Air or other fluid from air inlet C may not pass distally past middle rotation seal 150 because notch 151 is not aligned with air inlet C. Thus, in the second configuration, only water or other fluid may exit only through air outlet D to be flushed through an air channel of an endoscope and clear the air channel of debris following a procedure.

In the second configuration, if a user is not operating cap 118 of valve 100, valve 100 may remain for a time in the second configuration due to an interaction between the spring 182 and the cap seal 190. Over a period of time (e.g., a predetermined period of time), a restorative force of spring 182 may return valve 100 to the first configuration. For example, cap seal 190 may exert forces opposite forces exerted by spring 182, thereby delaying relaxation of the spring 182 and return to the first configuration of the valve 100. Valve 100 may progressively be returned to the first configuration (e.g., it may slowly move from the second configuration to the first configuration). Because the proximal rotation seal 140 and the distal rotation seal 142 may each have a recessed notch (such as notch 212) adjacent to holes 146 and 148, respectively, water or other fluid may continue to flow through holes 146 and 148 even after hole 146 is no longer directly aligned with air outlet D and hole 148 is no longer directly aligned with water inlet A. For example, the notches may extend around a portion of a circumference of proximal rotation seal 140 and/or distal rotation seal 142 so that, as rotation seal 140 or 142 rotates along with valve stem 116, the notch may continue to be adjacent to air outlet D or water inlet A. Water or other fluid may flow from water inlet A, into the notch of distal rotation seal 142, into hole 146, through distal opening 132, through lumen 122, through proximal opening 130, out of hole 148, through the notch of proximal rotation seal 140, and into water outlet D. Water or other fluid may cease to flow when the notches of proximal rotation seal 140 and/or distal rotation seal 142 are no longer in communication with air outlet D and/or water inlet A, respectively. Thus, valve 100 may deliver water to air outlet D for a predetermined amount of time, which may be specified by a cleaning protocol. For example, cap seal 190 and spring 182 may be calibrated so as to flush an air channel for a particular, predetermined amount of time An exemplary method for using valve 100 is provided herein. Following a procedure with an endoscope, the endoscope may be removed from a patient. In order to prepare the endoscope for reprocessing, an air/water valve may be removed from valve cylinder 139. Valve 100 may then be inserted into valve cylinder 139 while valve 100 is in the first configuration. In the first configuration, as discussed above, neither air nor water may be flushed through any channel of the endoscope. A user may rotate rotatable portion 172 of cap 118 to transition valve 100 to the second configuration. The user may then release rotatable portion 172 of cap 118 and may attend to other aspects of a post-operative procedure. Even after rotatable portion 172 is released, water or other fluid may continue to flow for a predetermined time from water inlet A and out of air outlet D, through the air channel of the endoscope. After valve 100 has flushed water or other fluid through the air channel for the predetermined amount of time, the valve 100 may be removed from valve cylinder 139 and may optionally be disposed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical valve comprising:
a valve stem having a closed proximal end face and a lumen having a proximal opening and a distal opening; and
an operation portion, including:
a stationary portion; and
a movable portion, wherein the movable portion is movable relative to the stationary portion and fixed relative to the valve stem;
wherein, in a first configuration of the medical valve, a first fluid flows into the medical valve via a second inlet of a valve cylinder and out of the medical valve via a first outlet of the valve cylinder and a second outlet of the valve cylinder;
wherein, in a second configuration of the medical valve, a second fluid flows into the medical valve via a first inlet of the valve cylinder and out of the medical valve via the second outlet of the valve cylinder;
wherein, in the first configuration, the proximal opening of the lumen is rotationally offset from the second outlet and the distal opening of the lumen is rotationally offset from the first inlet; and
wherein, in the second configuration, the proximal opening of the lumen is aligned with the second outlet and the distal opening of the lumen is aligned with the first inlet.

2. The medical valve of claim 1, wherein the first fluid is air, and wherein the second fluid is liquid.

3. The medical valve of claim 1, wherein, in the second configuration, the second fluid flows out of the medical valve only via the second outlet of the valve cylinder.

4. The medical valve of claim 1, wherein a first seal is axially aligned with the first inlet and the distal opening of the lumen, wherein the first seal includes a first hole formed through a wall of the first seal, wherein the first hole is aligned with the distal opening of the lumen, and wherein, in the second configuration, the first hole is aligned with the first inlet.

5. The medical valve of claim 4, wherein a second seal is axially aligned with the second inlet, wherein the second seal includes a notch, wherein the notch extends along a longitudinal length of the second seal, wherein, in the first configuration, the notch is aligned with the second inlet, and wherein, in the second configuration, the notch is rotationally offset from the second inlet.

6. The medical valve of claim 5, wherein a third seal is axially aligned with the second outlet and the proximal opening of the lumen, wherein the third seal includes a second hole formed through a wall of the third seal, wherein the second hole is aligned with the proximal opening of the lumen, and wherein, in the second configuration, the second hole is aligned with the second outlet in the second configuration.

7. A medical valve comprising:
a valve stem including a lumen having a proximal opening and a distal opening, wherein rotation of the valve stem about a longitudinal axis of the valve stem transitions the medical valve from a first configuration to a second configuration;
a first seal disposed on the valve stem;
a second seal disposed on the valve stem;
a third seal disposed on the valve stem;
a stationary portion;
a movable portion fixed to the valve stem and configured to be movable relative to a valve cylinder; and
a biasing member disposed between the stationary portion and the movable portion, wherein the biasing member is configured to rotate the movable portion about the longitudinal axis and bias the medical valve from the second configuration toward the first configuration,
wherein the medical valve is configured to be inserted into the valve cylinder such that a water inlet of the valve cylinder is axially aligned with the first seal, an air inlet of the valve cylinder is axially aligned with the second seal, and an air outlet of the valve cylinder is axially aligned with the third seal,
wherein, in the first configuration of the medical valve, a first fluid flows into the medical valve via the air inlet and out of the medical valve via the air outlet and a water outlet of the valve cylinder;
wherein, in the first configuration, the first fluid does not flow through the valve stem; and
wherein, in the second configuration of the medical valve, a second fluid flows into the medical valve via the water inlet and out of the medical valve via the air outlet.

8. The medical valve of claim 7,
wherein the first seal includes a first recessed notch extending partially around an outer circumference of the first seal and a first hole within the first recessed notch of the first seal, wherein, in the first configuration, the first hole is rotationally offset from the water inlet, wherein, in the second configuration, the first hole is aligned with the water inlet,
wherein the third seal includes a second recessed notch extending partially around an outer circumference of the third seal and a second hole within the second recessed notch, wherein, in the first configuration, the second hole is rotationally offset from the air outlet, and wherein, in the second configuration, the second hole is aligned with the air outlet.

9. The medical valve of claim 8, wherein, in the first configuration, the proximal opening is rotationally offset from the air outlet and the distal opening is rotationally offset from the water inlet, wherein, in the second configuration, the proximal opening is aligned with the air outlet and the distal opening is aligned with the water inlet, wherein the first hole of the first seal is aligned with the distal opening of the lumen, and wherein the second hole of the third seal is aligned with the proximal opening of the lumen.

10. The medical valve of claim 7, wherein the second seal includes a third recessed notch extending along a longitudinal length of the third seal, wherein, in the first configuration, the third recessed notch is aligned with the air inlet, and wherein, in the second configuration, the third recessed notch is rotationally offset from the air inlet.

11. The medical valve of claim 7, wherein, in the second configuration, the second fluid flows out of the medical valve via only the air outlet.

12. The medical valve of claim 7, wherein the biasing member includes a torsion spring configured to rotate the movable portion about the longitudinal axis and bias the medical valve toward the first configuration.

13. A medical valve comprising:
a valve stem including a lumen having a proximal opening and a distal opening,
wherein rotation of the valve stem about a longitudinal axis of the valve stem transitions the medical valve from a first configuration to a second configuration, wherein the valve stem is configured to be received within a valve cylinder having a first inlet, a first outlet, a second inlet, and a second outlet;

a first seal disposed on the valve stem, wherein the first seal is configured to be axially aligned with the first inlet; and a second seal disposed on the valve stem, wherein the second seal is configured to be axially aligned with the second outlet;

wherein, in the first configuration of the medical valve, a first fluid flows into the medical valve via the second inlet of the valve cylinder and out of the medical valve via the first outlet;

wherein, in the first configuration, the first fluid does not flow through the valve stem; and wherein, in the second configuration of the medical valve, a second fluid flows into the medical valve via the first inlet of the valve cylinder and out of the medical valve via the second outlet of the valve cylinder.

14. The medical valve of claim 13, wherein the first seal includes a first hole formed through a wall of the first seal, wherein the second seal includes a second hole formed through a wall of the second seal, wherein, in the first configuration, the first hole and the second hole each face a first direction, wherein, in the second configuration, the first hole and the second hole each face a second direction, and wherein the first direction differs from the second direction.

15. The medical valve of claim 14, wherein the first hole of the first seal is aligned with the distal opening of the lumen, and wherein the second hole of the second seal is aligned with the proximal opening of the lumen.

16. The medical valve of claim 13, further comprising:
a stationary portion fixed relative to the valve cylinder;
a movable portion fixed to the valve stem and movable relative to the stationary portion, wherein the movable portion is configured to rotate the valve stem in a first direction about the longitudinal axis from the first configuration into the second configuration; and
a biasing member disposed between the stationary portion and the movable portion, wherein the biasing member includes a torsion spring configured to rotate the movable portion in a second direction about the longitudinal axis opposite the first direction, which in turn rotates the valve stem in the second direction to bias the medical valve from the second configuration toward the first configuration.

17. The medical valve of claim 1, wherein the operation portion further includes a biasing member disposed between the stationary portion and the movable portion, wherein the biasing member is configured to bias the medical valve from the second configuration toward the first configuration.

18. The medical valve of claim 17, wherein the biasing member includes a torsion spring configured to rotate the movable portion about a longitudinal axis and bias the medical valve toward the first configuration.

19. The medical valve of claim 1, wherein, in the first configuration of the medical valve, the first fluid does not flow through the lumen of the valve stem.

20. The medical valve of claim 1, wherein rotation of the valve stem about a longitudinal axis of the valve stem transitions the medical valve from the first configuration to the second configuration.

* * * * *